US00PP25528P2

(12) United States Plant Patent
Kordes

(10) Patent No.: US PP25,528 P2
(45) Date of Patent: May 12, 2015

(54) HYBRID TEA ROSE PLANT NAMED 'KORDIAGRAF'

(50) Latin Name: *Rosa hybrida*
Varietal Denomination: KORdiagraf

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Schöne Rosenschulen GmbH & Co KG, Offenseth-Sparrieshoop (DE)

( * ) Notice: Subject to any disclaimer, the term of this patent is extended or adjusted under 35 U.S.C. 154(b) by 112 days.

(21) Appl. No.: 13/987,438

(22) Filed: Jul. 24, 2013

(51) Int. Cl.
*A01H 5/00* (2006.01)

(52) U.S. Cl.
USPC ..... Plt./130

(58) Field of Classification Search
USPC ..... Plt./130, 132
See application file for complete search history.

*Primary Examiner* — Kent L Bell

(57) ABSTRACT

A new and distinct variety of rose with long lasting, novel violet red flowers, and attractive foliage with excellent disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORdiagraf'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2003. The crossing was between an 'un-named seedling', the seed parent, and another 'un-named seedling', the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORdiagraf'.

SUMMARY OF THE INVENTION

The new rose plant may be distinguished from its seed parent, an 'un-named seedling', by the following combination of characteristics:

1. 'KORdiagraf' has violet red flowers, whereas the 'un-named seedling' has lavender pink.
2. 'KORdiagraf' has excellent disease resistance, whereas the 'un-named seedling' has poor disease resistance.

The new rose plant may be distinguished from its pollen parent, an 'un-named seedling', by the following combination of characteristics:

1. 'KORdiagraf' has a very double petal count, whereas the 'un-named seedling' has a semi-double petal count.
2. 'KORdiagraf' generally has one flower per stem, whereas the 'un-named seedling' flowers in clusters.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORdiagraf' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORdiagraf' was selected in May 2004 from the seedling beds to be asexually propagated for further evaluation. The first asexual propagation of 'KORdiagraf' was done by budding in July 2004 at the inventor's nursery in Offenseth-Sparrieshoop, Germany.

These initial and other subsequent propagations conducted in controlled environments demonstrate that 'KORdiagraf' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORdiagraf'.

DETAILED BOTANICAL DESCRIPTION

The following is a description of 'KORdiagraf', as observed growing in June 2013 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORcoluma', a rose variety from the same inventor described and illustrated in U.S. Plant Pat. No. 17,047 and issued on Aug. 22, 2006 are compared to 'KORdiagraf' in Chart 1.

CHART 1

| Characteristic | 'KORdiagraf' | 'KORcoluma' |
|---|---|---|
| Blooming habit | Continuous | Recurrent |
| Fragrance | Strong | Light to moderate |
| Flower color, general tonality | Red-Purple Group 61A | Red Group 46B |

Parents:

*Seed parent*.—An 'un-named seedling'.

*Pollen parent*.—An 'un-named seedling'.

Classification:

*Botanical classification*.—*Rosa hybrida* 'KORdiagraf'.

*Commercial classification*.—Hybrid Tea rose.

FLOWER AND FLOWER BUD

Blooming habit: Continuous.

Flower bud:

*Size*.—Upon opening, 25 mm in length from base of receptacle to distal end of bud and 20 mm diameter at its widest point.

*Bud form*.—Medium. Pointed ovoid.

*Bud color*.—As sepals first unfold, bud color is Greyed-Purple Group N186A. When ¼ open, the upper surface of petals is Red-Purple Group 59A, Red-Purple Group 59B and Red-Purple Group 59C with intonations of Greyed-Purple Group N186B; and the lower surface is Greyed-Purple Group 187A, Greyed-Purple Group 187C and Greyed-Purple Group N186B.

*Sepals*.—Color: Upper surface: Green Group 143A. Lower surface: Yellow-Green Group 144A. Size: Average 30-40 mm (l)×12-14 mm (w). Shape: Strong foliaceous appendages on 3 of the five sepals. Apex: Cirrose. Base: Flat at union with receptacle. Quantity: Five. Surface texture: Upper side: Moderately pubescent. Lower surface: Abundant stipitate glands. Margins: With numerous stipitate glands.

Flower bloom:

*Fragrance*.—Strong.

*Duration*.—On the plant 3-4 days. As a cut flower, 3 days. Senesced petals drop away cleanly.

*Size*.—Medium for a hybrid tea rose. When open, the average flower diameter is 90-100 mm and the average flower height is 50-55 mm.

*Form*.—Shape of flower when viewed from the side: Upon opening, upper part: Flattened convex. Upon opening, lower part: Flattened convex. Open flower, upper part: Flattened convex. Open flower, lower part: Concave.

Color:

*Upon opening, petals*.—Outermost petals: Outer Side: Greyed-Purple Group 71A and Greyed-Purple Group. Inner Side: Purple Group N79A, Purple Group N79B and Purple Group N79C. Innermost petals: Outer Side: Red-Purple Group 60A and Red-Purple Group 58A. Inner Side: Greyed-Purple Group N186B.

*Upon opening, basal petal spots*.—Basal petal spot, outermost petals: Outer Side: Green-White Group 157D. Inner Side: Greyed-White Group 156D. Basal petal spot, innermost petals: Outer Side: White Group N 155D. Inner Side: Green-White Group 157D.

*After opening, petals*.—Outermost petals: Outer Side: Greyed-Purple Group 64A and Greyed-Purple Group 64B. Inner Side: Purple Group N79B and Red-Purple Group 61B. Innermost petals: Outer Side: Red-Purple Group 61B. Inner Side: Red-Purple Group 59C. Occasional stripe in center of petal White Group 155A.

*After opening, basal petal spots*.—Basal petal spot, outermost petals: Outer Side: No distinctive coloration at petal base observed. Inner Side: White Group N155B. Basal petal spot, innermost petals: Outer Side: White Group 155C. Inner Side: White Group 155B.

General tonality: On open flower Red-Purple Group 61A. No change in the general tonality at the end of the 3$^{rd}$ day. Afterwards, general tonality is Purple Group N79C.

Petals:

*Petal count*.—Very Double.

*Average range*.—Approximately 65-70 petals under normal conditions.

*Petal reflex*.—Petals reflex somewhat.

*Petal margin*.—Entire.

*Petal shape*.—Obovate. Apex: Obtuse. Base: Attenuate.

*Petal size*.—25-40 mm (l)×25-40 mm (w).

*Thickness*.—Average.

*Petal arrangement*.—Not formal.

*Texture*.—Smooth.

Petaloids:

*Petaloid count*.—Average of 18-20 per flower.

*Petaloid size*.—10-20 mm (l)×5-20 mm (w).

*Petaloid color*.—Inner side: Red-Purple Group 60A with center stripe White Group 155B. Outer side: Red-Purple Group 60B with center stripe White Group 155B.

*Petaloid texture*.—Leathery.

*Margins*.—Entire to indented, with some highly irregular.

*Petaloid shape*.—Most commonly oval to spatulate. Apex: Obtuse. Base: Attenuate to obtuse.

Reproductive organs:

*Pistils*.—Average. Approximately 40 present. Stigmas: Location: Slightly superior in position to anthers. Color: Green-White Group 157A. Styles: Length: About 10 mm long. Color: Green-White Group 157B. Intonations of Red-Purple Group N66A.

*Stamens*.—Approximately 65 on average and regularly arranged. Anthers: Size: Average 2 mm (l)×1 mm (w). Pollen: Generally present. Color: Greyed-Orange Group N163C. Filaments: Color: Green-White Group 157B. Length: 9 mm.

*Receptacle*.—Surface: With light pubescence and stipitate glands. Color: Yellow-Green Group 146C. Intonations of Greyed-Purple Group 183B. Shape: Funnel-shaped. Texture: Smooth. Size: 18 mm (h)×15 mm (w).

*Peduncle*.—Surface: With numerous stipitate glands. Length: 50-70 mm average length. Diameter: 4-5 mm average diameter. Color: Yellow-Green Group 146C. Intonations of Greyed-Purple Group 183C. Strength: Very strong. Texture: Smooth. Borne: Mostly singularly. Sometimes multiple flower buds per stem, with 2 to 3. Flowers held upright.

THE PLANT

*Growth*.—Moderately vigorous growth.

*Plant habit*.—Upright to bushy. When grown as a field plant, the average plant height is 120 cm and the average plant width is 100 cm.

*Stems*.—Stem color: Young wood: Yellow-Green Group 146B. Older wood: Yellow-Green Group 146B. Intonations: Greyed-Purple Group 183B. Stem surface texture: Young wood: Smooth. Older wood: Rough.

*Prickles*.—Present. Incidence: Average of 10 per each 10 cm of stem. Size: Average length: 8 mm. Color: Immature prickles: Greyed-Purple Group 183A. Mature prickles: Greyed-Orange Group 163D. Shape: Concave.

*Leaves*.—Normally 5 leaflets on normal leaves in middle of the stem. Venation pattern: Pyramidal net pattern. Leaf size: 150 mm (l)×110 mm (w). Abundance: Average.

*Leaflets*.—Size: Average size of the terminal leaflet is 75 mm (l)×50 mm (w). Shape: Elliptic. Base: Obtuse. Apex: Apiculate. Margins: Finely serrated. Surface: Upper side of leaflet: Semi-glossy. Under side of leaflet: Matte. Texture: Upper side of leaflet: Smooth. Under side of leaflet: Smooth. Color, mature foliage: Upper Leaflet Surface: Green Group 139A. Lower Leaflet Surface: Yellow-Green Group 147B. Color, juvenile foliage: Upper Leaflet Surface: Green Group 137A. Lower Leaflet Surface: Yellow-Green Group 147B. Anthocyanin intonation: Greyed-Purple Group 187A and Greyed-Purple Group 187B. Location: Juvenile foliage. Arrangement: Odd pinnate. Venation: Reticulate.

*Stipules*.—Surface: Occasional prickles on lower side of stipule. Size: 22 mm (l)×5 mm (w). Stipule color: Yellow-Green Group 146A. Anthocyanin: Greyed-Purple Group 183D, center of upper side. Stipitate glands: Limited along margins. Texture: Smooth. Shape: Apex: Apiculate. Base: Winged.

*Petiole*.—Length: Average 25 mm. Diameter: Average 3 mm. Petiole color: Yellow-Green Group 146B. Underneath: Yellow-Green Group 146C. Margins: With abundant stipitate glands. Anthocyanin: Greyed-Purple Group 188D, occasionally on upper side of margins. Prickles: Present on lower side. Texture: Smooth.

*Petiole rachis*.—Length: Average 20 mm. Diameter: Average 3 mm. Color: Yellow-Green Group 146B. Anthocyanin: Greyed-Purple Group 183D on upper side. Margins: With limited stipitate glands. Prickles: A few small prickles underneath, typically at leaflet attachment. Texture: Smooth.

Hips/seed formation: None observed.

Winter hardiness: To date, the variety has been grown successfully in Zone 5B to 9A.

Disease resistance: Excellent resistance to Powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

* * * * *

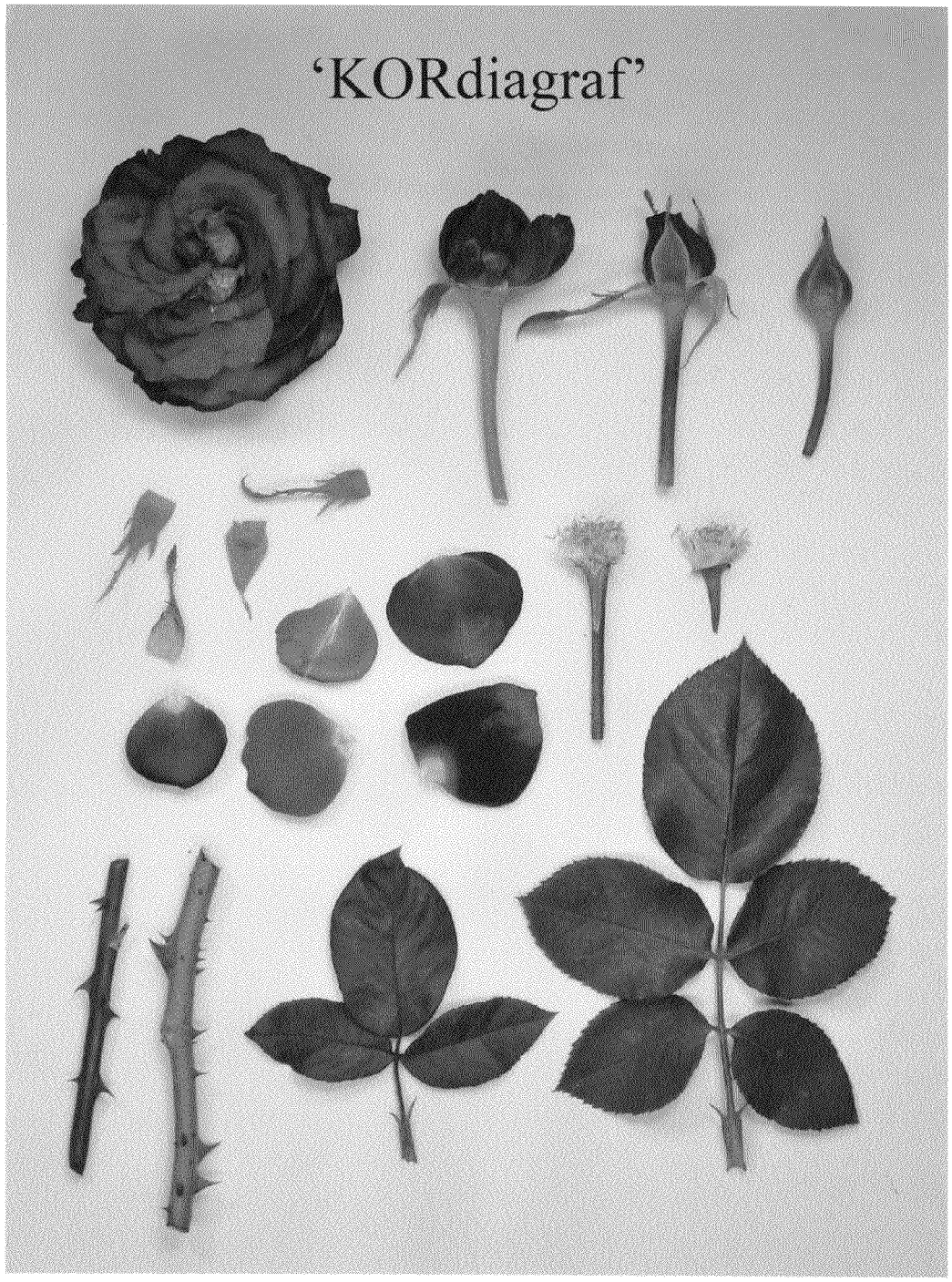
'KORdiagraf'